United States Patent
Moeskops

(10) Patent No.: US 11,311,335 B2
(45) Date of Patent: Apr. 26, 2022

(54) OPTICAL SYSTEM

(71) Applicant: KONINKLIJKE PHILIPS N.V., Eindhoven (NL)

(72) Inventor: Bastiaan Wilhelmus Maria Moeskops, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 291 days.

(21) Appl. No.: 15/570,515

(22) PCT Filed: Apr. 25, 2016

(86) PCT No.: PCT/EP2016/059120
§ 371 (c)(1),
(2) Date: Oct. 30, 2017

(87) PCT Pub. No.: WO2016/177589
PCT Pub. Date: Nov. 10, 2016

(65) Prior Publication Data
US 2018/0140357 A1 May 24, 2018

(30) Foreign Application Priority Data
May 7, 2015 (EP) ..................................... 15166752

(51) Int. Cl.
*A61B 18/20* (2006.01)
*A61B 18/00* (2006.01)

(52) U.S. Cl.
CPC .. *A61B 18/203* (2013.01); *A61B 2018/00452* (2013.01); *A61B 2018/00476* (2013.01);
(Continued)

(58) Field of Classification Search
None
See application file for complete search history.

(56) References Cited

U.S. PATENT DOCUMENTS 5,533,266 A * 7/1996 Kelman ............... A61B 18/203
132/200
5,993,440 A * 11/1999 Ghassemi ............... B26B 19/00
30/41.5
(Continued)

FOREIGN PATENT DOCUMENTS

DE 19916653 A1 10/2000
JP 2002291764 10/2002
(Continued)

OTHER PUBLICATIONS https://www.myalcon.com/products/surgical/wavelight-allegretto-wave-eye-q-laser/perfectpulse.shtml.

*Primary Examiner* — Michael W Kahelin
*Assistant Examiner* — Elizabeth K So

(57) ABSTRACT

The present application relates to an optical system (1) comprising a plurality of optical components, a pulse generating arrangement (3) configured to generate a treatment pulse along a treatment pulse optical path through said optical components, said pulse generating arrangement also being configured to generate a probe pulse along a probe pulse optical path extending through said optical components, a sensor (8) configured to generate information indicative of an optical characteristic of said probe pulse that has passed along said probe pulse optical path through said optical components, and a controller (5) configured to control said pulse generating apparatus (3) to selectively emit said treatment pulse along said treatment pulse optical path (2), in dependence on the information generated by the sensor (8).

20 Claims, 2 Drawing Sheets

(52) U.S. Cl.
CPC ........... *A61B 2018/00708* (2013.01); *A61B 2018/00785* (2013.01)

(56) References Cited

U.S. PATENT DOCUMENTS

| | | | |
|---|---|---|---|
| 6,676,654 B1 | 1/2004 | Balle-Petersen | |
| 2003/0091087 A1* | 5/2003 | Ershov | H01S 3/223 372/55 |
| 2006/0041289 A1 | 2/2006 | Cense | |
| 2006/0178659 A1* | 8/2006 | Van Hal | A61B 18/203 606/2 |
| 2006/0200114 A1 | 9/2006 | Ferren | |
| 2012/0140231 A1* | 6/2012 | Knox | G01N 15/1434 356/442 |

FOREIGN PATENT DOCUMENTS

| | | |
|---|---|---|
| WO | 95/33600 | 12/1995 |
| WO | 2015051999 A1 | 4/2015 |

\* cited by examiner

OPTICAL SYSTEM

This application is the U.S. National Phase application under 35 U.S.C. § 371 of International Application No. PCT/EP2016/059120, filed on Apr. 25, 2016, which claims the benefit of International Application No. 15166752.4 filed on May 7, 2015. These applications are hereby incorporated by reference herein.

FIELD OF THE INVENTION

The present invention relates to an optical system, in particular, an optical system having a probe pulse to determine the condition of an optical path. The present invention also relates to a laser treatment device comprising the optical system. The present invention further relates to a method for using the laser treatment device.

BACKGROUND OF THE INVENTION

Conventional technologies for the treatment of hair and skin include arrangements of mechanical blades and abrasives which are placed against and dragged across a skin surface to cut hair or remove dead skin, respectively. However, these conventional technologies are harsh on the skin surface and cause damage or irritation.

It is known to use a laser beam to sever hair or treat skin as an alternative to mechanical blades and abrasives. Laser beam treatments are preferred because they do not require moving cutting parts or abrasive surfaces to be placed against the skin or hair. Therefore, the problem of skin surface damage or irritation is reduced. Furthermore, the problem of cutting elements becoming blunt and abrasives becoming smooth is eliminated.

It is also known that laser beams can themselves cause damage and irritation if the high intensity portion contacts the skin surface. Traditional optical systems will deactivate the laser beam if the skin surface extends too close to the high intensity portion of the laser beam. However, optical systems can become contaminated and the trajectory of the laser beam altered from its intended path. This can result in the laser beam being directed onto the wrong areas of the skin surface and/or causing damage and irritation to the skin surface.

SUMMARY OF THE INVENTION

It is an object of the invention to provide an optical system which substantially alleviates or overcomes the problems mentioned above.

According to the present invention, there is provided an optical system comprising a plurality of optical components, a pulse generating arrangement configured to generate a treatment pulse along a treatment pulse optical path through said optical components, said pulse generating arrangement also being configured to generate a probe pulse along a probe pulse optical path extending through said optical components, a sensor configured to generate information indicative of an optical characteristic of said probe pulse that has passed along said probe pulse optical path through said optical components, and a controller configured to control said pulse generating arrangement to selectively emit said treatment pulse along said treatment pulse optical path, in dependence on the information generated by said sensor.

Therefore, the optical system only emits a treatment pulse in dependence upon information generated by a sensor relating to a probe pulse.

The information generated by said at least one sensor may be indicative of any obstructions in said treatment pulse optical path.

The at least one sensor may be configured to generate information indicative of at least one characteristic of the probe pulse. The at least one characteristic may be, for example, but not limited to, the position of a taken altered probe pulse optical path through the optical system, the intensity, power, energy, spatial distribution or temporal distribution of the probe pulse. In some embodiments, if one or more of the sensed characteristics is not in accordance with a predetermined value or range of values, then the controller will not emit a treatment pulse.

Therefore, if the information, generated by the at least one sensor and indicative of the at least one probe pulse, indicates that the condition of the treatment pulse optical path is not satisfactory, i.e. the trajectory has been altered and the probe pulse contacts the skin surface, the treatment pulse will not be released. Consequently, the damage or irritation to the skin surface is reduced by the optical system.

The treatment pulse may be configured to treat skin and/or sever hair and has a pulse energy which may be greater than the pulse energy of said probe pulse.

Therefore, the optical system reduces any damage or irritation caused to the skin surface by ensuring that the lower intensity pulse is the only pulse which may contact the skin surface.

The pulse energy of said probe pulse may not be sufficient to harm a skin surface.

Therefore, the optical system may completely eliminate or at least significantly reduce the possibility of the skin surface being damaged or irritated.

The probe pulse optical path may be configured to coincide with at least part of said treatment pulse optical path. Alternatively, the probe pulse optical path can be a different optical path to the treatment pulse optical path. For example, the probe pulse optical path can extend substantially parallel to the treatment pulse optical path.

If the probe pulse and treatment pulse coincide, the probe pulse is able to verify the condition of the exact treatment pulse optical path taken by the treatment pulse. Because there is no difference in the optical path of the probe pulse and the treatment pulse the error in the determination of the condition of the treatment pulse's optical path may be eliminated or at least significantly reduced.

The probe pulse optical path may be substantially along the optical path or parallel to it to determine the condition of the optical path. Therefore, the probe pulse optical path may be shorter than the treatment pulse optical path. The probe pulse optical path may be arranged to focus on a specific portion of the treatment pulse optical path rather than the whole treatment pulse optical path.

The pulse generating arrangement may comprise a treatment pulse generator configured to generate said treatment pulse and a probe pulse generator configured to generate said probe pulse.

Therefore, the optical system requires fewer components and can help to minimise the size of devices in which it is used. It also makes it easier to ensure the probe pulse travels along the same optical path as the treatment pulse.

The pulse generator may be configured to generate the treatment pulse within 10 ms, or more preferably, less than 1 ms, of the probe pulse.

Therefore, the delay between the probe pulse and the treatment pulse is sufficiently small to guarantee that environmental influence on the treatment pulse optical path in between the pulses is negligible.

The pulse generator may be configured to generate successive probe pulses with a time gap of less than 10 ms.

Therefore, the optical system is able to provide at least 10 probe pulses per second along the probe pulse optical path. The greater number of probe pulses potentially leads to a greater number of treatment pulses being released which can help to reduce the time taken to perform a treatment. Furthermore, the greater number of probe pulses results in a quicker identification of an obstruction on the treatment pulse optical path.

The controller may be configured to compare the characteristic measured by the sensor to a predetermined value and to emit the treatment pulse if the sensed characteristic matches the predetermined value.

Therefore, analysis of the probe pulse can be performed quickly to ensure that the treatment pulse is only generated if the probe pulse verifies that the condition of the treatment pulse optical path, or optionally the probe pulse optical path indicative of the treatment pulse optical path, is completely uninterrupted or unaltered.

If the at least one determined characteristic of the probe pulse matches the intended value of the at least one characteristic then the controller activates the laser pulse generating arrangement to generate the treatment pulse. The at least one determined characteristic of the probe pulse will match the intended value if the optical path is not obstructed, interrupted or altered by an obstruction.

The controller can be configured to compare the characteristic measured by the sensor to a predetermined range and to emit the treatment pulse if the sensed characteristic falls within said predetermined range.

Therefore, the treatment pulse is only generated if the probe pulse verifies that the condition of the treatment pulse optical path, or optionally the probe pulse optical path indicative of the treatment pulse optical path, is within a defined range. This means that the treatment pulse may be released even if there is an insignificant alteration or interruption to the treatment pulse optical path. Therefore, minor alterations or interruptions in the treatment pulse optical path do not prevent the treatment pulse from being generated as long as the skin surface or other components of the optical system are not damaged or irritated.

The sensor may be at the end of said probe pulse optical path.

Therefore, the probe pulse is able to travel along the whole of the treatment pulse optical path, or optionally the probe pulse optical path indicative of the treatment pulse optical path. This ensures that the probe pulse verifies the condition of the entire length of the optical path of the treatment pulse, or optionally of the probe pulse indicative of the treatment pulse optical path, and ensures that there is no interruption or alteration along the entire treatment pulse optical path. This helps to reduce the likelihood of a treatment pulse damaging or irritating the skin surface or other components of the optical system.

According to another aspect of the present invention, there is provided a laser treatment device comprising said optical system according to an optical system of the present invention.

Therefore, the optical system can be used to cut hair or treat skin. The optical system may be programmed to know the difference between hair and/or skin and an obstruction. In shaving systems, the at least one sensor may be capable of generating information capable of identifying obstructions caused by hairs to be cut from other obstructions, such as skin surfaces or water droplets. For example, a multi-element imaging sensor may be able to identify hair and avoid false positives by comparing the cylindrical shape of a hair to the flat plane of a skin surface.

In an alternative example, the controller and an intensity sensor may know the intensity drop caused by a hair and will prevent the generation of the treatment pulse if the intensity drops below a predetermined level. In another alternative embodiment, the at least one sensor may measure the temporal profile of a characteristic. The temporal profile of hair will change quickly as the hair is cut, whilst skin or water droplet obstruction will remain in the probe pulse optical path for a longer amount of time. Therefore, the optical system may be able to distinguish hair from skin and/or obstructions.

In skin treatment systems, the at least one sensor may be a skin position sensor. The skin position sensor may be capable of generating information indicative of the skin surface's location and geometry. Variations in the skin surface's location and geometry occur in the order of milliseconds to seconds. The variations in spatial and temporal distributions may be used to distinguish the skin surface from hair and/or obstructions.

Furthermore, the at least one characteristic of the probe pulse may be determined before the section of the optical path in which hair and/or skin is placed. Therefore, a treatment pulse may be released to sever hair and/or treat skin.

However, the optical system is not limited to being used to cut hair and treat skin. Alternatively, the optical system may be used in any situation in which a probe pulse is emitted to check that there are no obstructions on the optical path before a hazardous treatment pulse is emitted along the optical path.

A part of said treatment pulse optical path may be across a recess in said laser treatment device, parallel to, and optionally spaced from, a plane that extends across said recess in which a skin engaging face lies.

Therefore, the probe and/or treatment pulses are at substantially the same distance from the skin surface as they travel across the recess. This means that they are not too close to the skin surface on one side of the recess and too far away on the other. This helps to reduce uneven performance by giving more uniform results.

According to another aspect of the present invention, there is provided a method for cutting hair using a laser shaving device, having a recess into which hair extends comprising, operating an optical system to direct a probe pulse along a probe pulse optical path extending through a plurality of optical components, generating information indicative of the condition of a treatment pulse optical path that also extends through said optical components by measuring a characteristic of said probe pulse using a sensor along said probe pulse optical path, comparing said information indicative of a characteristic of said probe pulse against a predetermined range, and emitting a treatment pulse along said treatment pulse optical path through said components to cut hair extending into said recess when said information indicative of the characteristic of said probe pulse falls within said predetermined range.

Therefore, the treatment pulse is not released if the condition of the treatment pulse optical path, or optionally the probe pulse optical path indicative of the treatment pulse optical path, is not satisfactory, i.e. the trajectory has been altered and the probe pulse contacts the skin surface. Consequently, the damage or irritation to the skin surface is reduced by the optical system.

According to another aspect of the present invention, there is provided a computer program comprising instructions which, when executed by at least one processor, cause the method according to the present invention to be performed.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
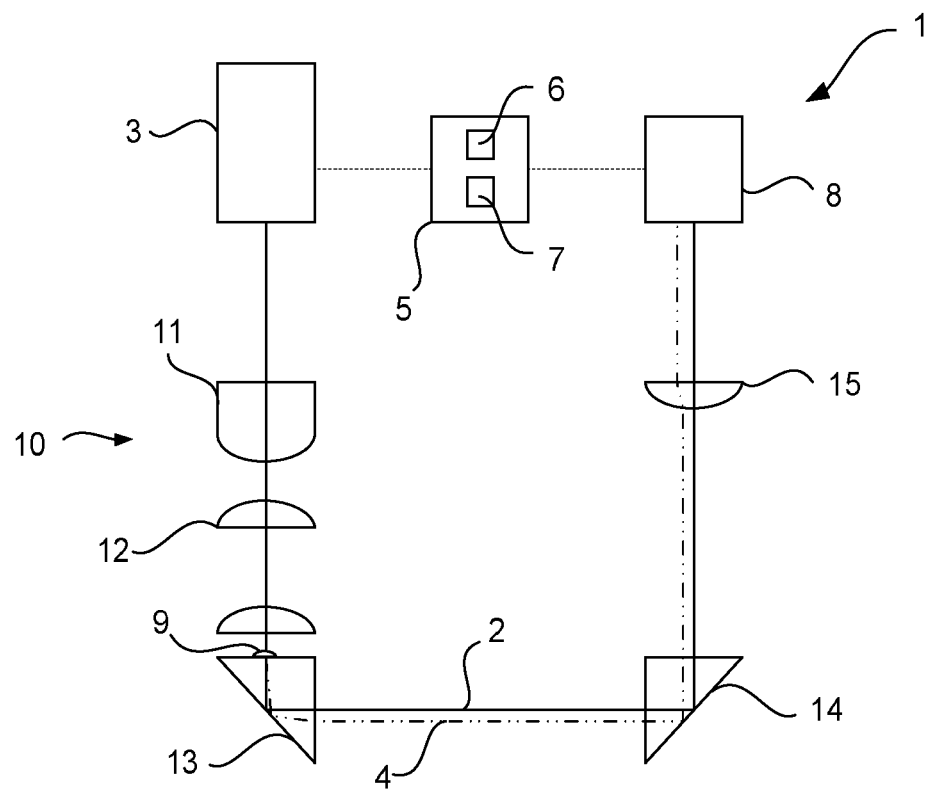
FIG. 1 shows a front view schematic diagram of an optical system.

Referring to FIG. 1, there is shown an optical system 1. The optical system 1 is configured to guide a laser pulse along an intended optical path 2. The intended optical path 2 is the route along which a laser pulse is intended to travel.

The optical system 1 comprises a laser pulse generating arrangement 3. The laser pulse generating arrangement 3 is configured to generate a treatment pulse and a probe pulse. Therefore, the laser pulse generating arrangement 3 is at the beginning of the intended optical path 2. The laser pulse generating arrangement 3 is configured to direct the laser pulses towards the rest of the optical system 1. The laser pulse generating arrangement 3 may be, for example, but not limited to, a laser diode.

In the present embodiment, the laser pulse generating arrangement 3 is configured to generate two different laser pulses. The first laser pulse is the probe pulse. The second laser pulse is the treatment pulse. The laser pulse generating arrangement 3 generates the pulses in sequence. That is, the probe pulse is generated before the treatment pulse. The treatment pulse travels along a treatment pulse optical path 2. The probe pulse travels along a probe pulse optical path (not shown). In the present embodiment, the probe pulse optical path is identical to and coincides with the treatment pulse optical path 2. Therefore, if the treatment pulse optical path 2 is uninterrupted and/or undisturbed the probe pulse and the treatment pulse will both travel along it. However, if the treatment pulse optical path 2 is disturbed then the probe pulse will travel along an altered optical path 4.

It will be understood that in an alternative embodiment, the laser pulse generating arrangement 3 of the optical system 1 may comprise individual laser pulse generators (not shown). In such an embodiment, the first laser pulse generator may generate the probe pulse and the second laser pulse generator may generate the treatment pulse. As the laser pulses originate from different sources, the probe pulse may only travel along an alternative probe pulse optical path (not shown). The alternative probe pulse optical path may be substantially the same as the treatment pulse optical path 2 of the treatment pulse. That is, the probe pulse may travel along the alternative probe pulse optical path, for example, but not limited to, parallel to and spaced from the treatment pulse optical path 2. This alternative path is a predetermined different path (not shown) for the probe pulse to the probe pulse optical path that coincides with the treatment pulse optical path 2.

The optical system 1 further comprises a controller 5. The controller 5 is configured to control the operation of the laser pulse generating arrangement 3. Therefore, the controller 5 controls the generation of the probe pulse and the treatment pulse. The controller 5 comprises a processor 6. The controller 5 further comprises a memory 7. The controller 5 is able to operate the optical system 1.

The processor 6 may take any suitable form. For instance, the processor 6 may be or include a microcontroller, plural microcontrollers, circuitry, a single processor, or plural processors. The controller 5 may be formed of one or multiple modules.

The memory 7 may take any suitable form. The memory 7 may include a non-volatile memory and/or RAM. The non-volatile memory may include read only memory (ROM), a hard disk drive (HDD) or a solid state drive (SSD). The memory 7 stores, amongst other things, an operating system. The memory 7 may be disposed remotely. The RAM is used by the processor 6 for the temporary storage of data.

The operating system may contain code which, when executed by the controller 5, controls the operation of the hardware components in the optical system 1.

The optical system 1 further comprises at least one sensor 8. In the present embodiment, the optical system comprises a single laser pulse sensor 8. The laser pulse sensor 8 may be an electronic sensor. Alternatively, the laser pulse sensor 8 may be a photodiode array. In the present embodiment, the laser pulse sensor 8 is configured to generate information indicative of at least one of the optical characteristics of the probe pulse which has traveled along the probe pulse optical path which coincides with the treatment pulse optical path 2.

In the present embodiment, one laser pulse sensor 8 is disposed at the end of the probe pulse optical path which coincides with the treatment pulse optical path 2. In an alternative embodiment, the laser pulse sensor 8 may be positioned at a different position along the probe pulse optical path. The laser pulse sensor 8 intersects the probe pulse optical path. Therefore, the probe pulse has to travel along the whole of the treatment pulse optical path 2 or substantially along it to be sensed by the laser pulse sensor 8. However, it will be understood that more than one laser pulse sensor 8 may be used.

The further along the probe pulse optical path the laser pulse sensor 8 is placed, the greater the proportion of the treatment pulse optical path 2, or the alternative probe pulse optical path indicative of the treatment pulse optical path, can be declared safe for the treatment pulse. Therefore, the safety of the optical system 1 is increased and the likelihood of damage or injury is reduced.

The laser pulse sensor 8 is configured to generate information indicative of at least one characteristic of the probe pulse. The at least one characteristic may be, for example, but not limited to, the position of the taken altered optical path 4 through the optical system 1, the intensity, power, energy, spatial distribution or temporal distribution of the probe pulse. The laser pulse sensor 8 is configured to communicate the information generated to the controller 5. The controller 5 uses the information generated by the laser pulse sensor 8 to determine the at least one characteristic, for example, the taken altered optical path 4 and/or the intensity of the probe pulse.

The controller 5 then compares the at least one determined characteristic of the probe pulse to the intended value of the at least one characteristic of the probe pulse. By comparing the at least one determined characteristic of the probe pulse to the intended value of the at least one characteristic the controller 5 can determine the quality of the treatment pulse optical path 2. If the at least one determined characteristic of the probe pulse matches the intended value of the at least one characteristic then the controller 5 activates the laser pulse generating arrangement 3 to generate the treatment pulse. The at least one determined characteristic of the probe pulse will match the intended value if the probe pulse optical path, which may coincide with the treatment pulse optical path 2, is not obstructed, interrupted or altered by an obstruction 9. The obstruction 9 may be a contaminant such as, for example, but not limited to detritus or the obstruction 9 may be a skin surface 22, shown in FIG. 3. The contaminant may be, for example, but not limited to, detritus and a water or sweat droplet. The contaminant may be on any surface of the optical system 1.

In the event that the at least one determined characteristic of the probe pulse does not match the intended values then the controller 5 does not activate the laser pulse generating arrangement 3. Therefore, the treatment pulse is not generated and does not travel through the optical system 1. The at least one determined characteristic of the probe pulse may not match the intended value if the treatment pulse optical path 2, or alternative probe pulse optical path indicative of the treatment pulse optical path 2, is contaminated by detritus or sweat(water) which refracts the probe pulse off course or is interrupted by detritus or a skin surface which blocks probe pulse.

In an alternative embodiment, the controller 5 may operate the laser pulse generating arrangement 3 to generate the treatment pulse if the at least one determined characteristic of the probe pulse is within a predetermined range of the intended values. The intended value may be a reference value that is programmed in the memory 7 of the controller 5. Alternatively, the reference level or intended value may be measured or defined after manufacturing by sending a probe pulse along the uncontaminated probe pulse optical path, which may coincide with the treatment pulse optical path 2. In another embodiment, the reference level or intended value may be set or updated by the user.

The predetermined range may be ±30%. That is, the at least one characteristic of the probe pulse may have to be within the range of up to ±30% of the intended value of said at least one characteristic of said probe pulse for the treatment pulse to be generated. More preferably, the predetermined range may be ±10%. Therefore, the at least one characteristic of the probe pulse may have to be within the range of up to ±10% of the intended value of said at least one characteristic of said probe pulse for the treatment pulse to be generated. Depending on the application of the optical system 1, the predetermined range that the at least one characteristic of the probe pulse has to be within of the intended value may be as little as ±5%, or even ±1%.

Figure 2:
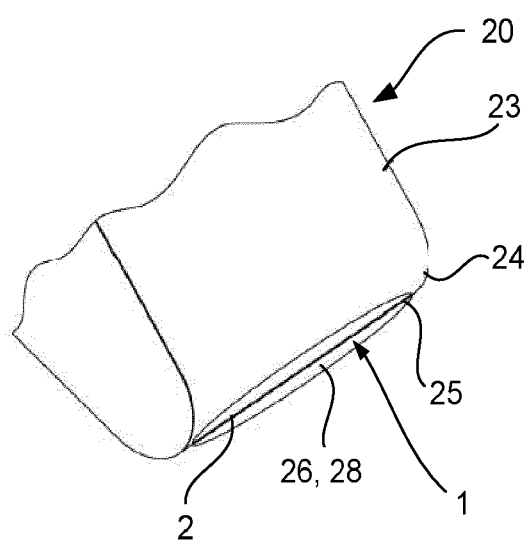
FIG. 2 shows a perspective view of a laser shaving device for treating hair or skin using a laser beam having a recess and comprising the optical system of FIG. 1.
Figure 3:
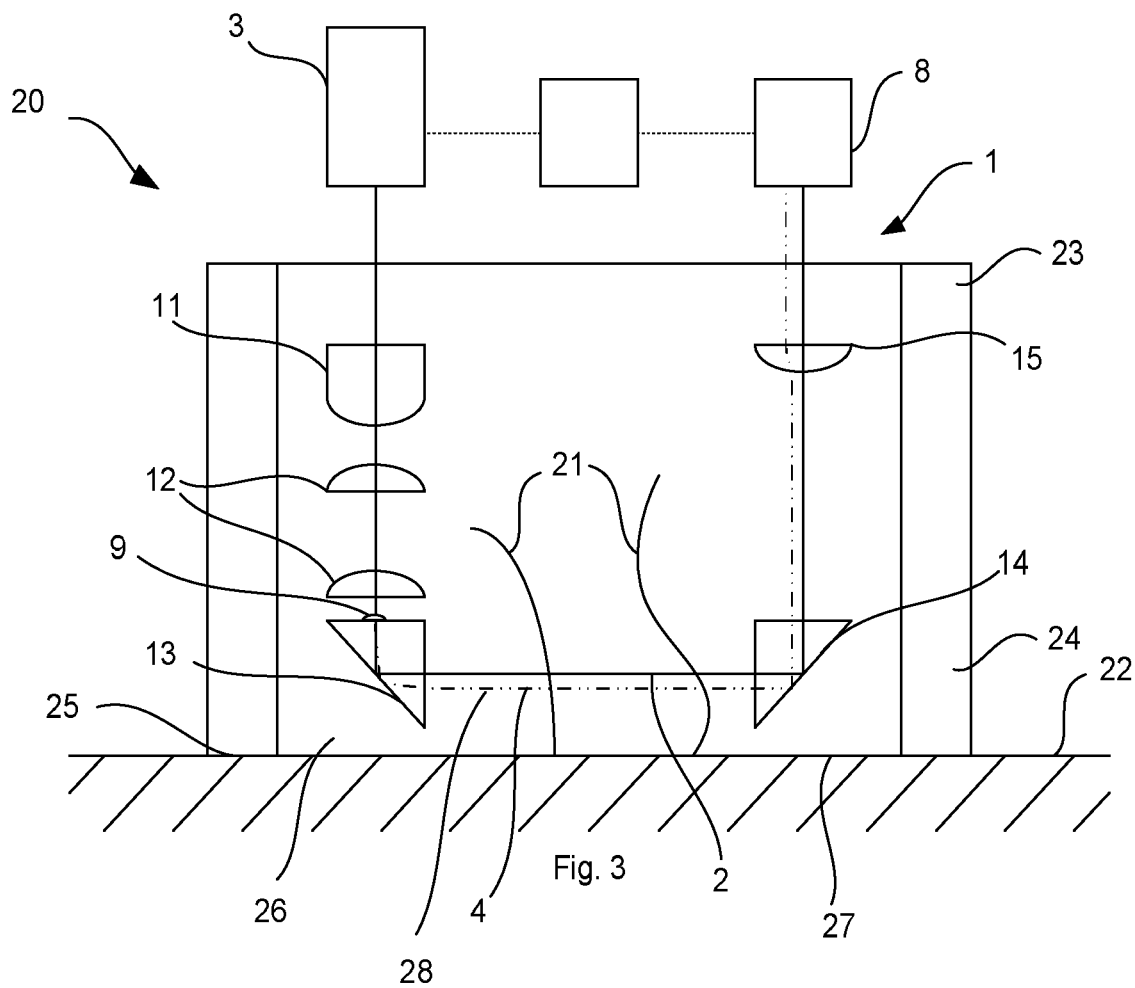
FIG. 3 shows a front view schematic diagram of the recess end of the laser shaving device for treating hair or skin using a laser beam.

In the present embodiment, the treatment pulse which is intended to travel along the treatment pulse optical path 2 through the optical system 2 has a pulse energy that is large enough to damage living tissue (not shown), and/or components of a device, an example of which can be seen in FIG. 2 and FIG. 3, comprising the optical system 1. Therefore, by preventing the generation and emission of the treatment pulse along the altered optical path 4, which may direct the high intensity treatment pulse onto living tissue undesired damage or irritation can be avoided. The pulse energy of the treatment pulse may be between 0.1 and $1 \times 10^3$ J. The intensity of the treatment pulse may be between $1 \times 10^4$ and $1 \times 10^{10}$ W/m².

The probe pulse which is emitted by the laser pulse generating arrangement 3 has a pulse energy which is less than the pulse energy of the treatment pulse. The pulse energy of the probe pulse may be between $1 \times 10^{-1}$ and 1 J. Therefore, even if the probe pulse optical path, which may coincide with the treatment pulse optical path 2, is contaminated so that the probe pulse is deflected along the altered optical path 4, the probe pulse will cause less damage or irritation to living tissue or components of a device comprising the optical system 1. The intensity of the probe pulse is low enough that the probe pulse cannot cause damage or irritation to living tissue or components of a device comprising the optical system 1. The intensity of the probe pulse may be between $1 \times 10^{-5}$ and $1 \times 10^7$ W/m². Therefore, no damage or irritation is caused by the optical system 1 when the probe pulse optical path and/or the treatment pulse optical path 2 is contaminated because the probe pulse is too weak and the treatment pulse is not generated and emitted.

The time delay between the release of the probe pulse and the subsequent treatment pulse, when the controller 5 determines that the condition of the treatment pulse optical path 2 is satisfactory, is less than 10 ms. More preferably, the time delay between the release of the probe pulse and the subsequent treatment pulse is less than 1 ms. Therefore, the time difference between analysing the condition of the treatment pulse optical path 2 and the emission of the treatment pulse is sufficiently small to ensure than environmental changes on the treatment optical path 2, i.e. position of the contaminant 9 or location of new contaminants, is minimal. Hence, if the treatment pulse is emitted from the laser pulse generating arrangement 3, it is more likely to successfully travel along the length of the treatment pulse optical path 2.

Furthermore, the time gap between subsequent probe pulses is less than 10 ms. Therefore, the condition of the probe pulse optical path which coincides with the treatment pulse optical path 2, or the alternative probe pulse optical path indicative of the treatment pulse optical path 2, is evaluated frequently to ensure that any environmental change along the treatment pulse optical path 2 is measured. This helps to guarantee that the treatment pulse does not travel through the optical system 1 if it may cause damage. Furthermore, it means that more treatment pulses may be emitted by the laser pulse generating arrangement 3 which can increase the speed of a procedure or task being performed using the optical system 1.

The optical system 1 may further comprise additional components configured to direct the laser pulses along the probe pulse optical path and/or the treatment pulse optical path 2. In the present embodiment, shown in FIG. 1, for example, the optical system 1 further comprises a lens arrangement 10. The lens arrangement 10 is configured to focus the laser pulses emitted from the laser pulse generating arrangement 3. In the present embodiment, the lens arrangement 10 comprises a collimating lens 11. The collimating lens 11 reduces or eliminates divergence of the laser pulses emitted from the laser pulse generating arrangement 3 towards the rest of the optical system 1. The lens arrangement 10 further comprises at least one focus lens 12. The present embodiment comprises two focus lenses 12 for converging and directing the collimated laser pulses.

The optical system 1 further comprises a first reflective element 13 and a second reflective element 14. The first and second reflective elements 13, 14 are configured to reflect an incident laser pulse along the probe pulse optical path and/or the treatment pulse optical path 2. However, it will be understood that in an alternative embodiment the optical system 1 may have an alternative number of reflective elements. The first and second reflective elements 13, 14 may comprises a mirror or prism or any other optically reflective surface.

The optical system 1 may further comprise an energy dissipater (not shown). The energy dissipater may be located at the laser pulse sensor 8. Therefore, a treatment pulse travelling along the treatment pulse optical path 2 will not cause damage to any of the components of the optical system 1. The optical system further comprises a detector lens 15 disposed on the probe pulse optical path and/or the treatment pulse optical path 2 prior to the laser pulse sensor 8. The detector lens 15 is configured to adjust the dimensions of the laser pulse to suit the laser pulse sensor 8. It will be understood that the detector lens 15 may be omitted.

In one embodiment, the optical system 1 may comprises an actuator (not shown) to adjust the probe pulse optical path and/or the treatment pulse optical path 2. Therefore, a user may select the treatment pulse optical path 2, which controls the degree of treatment, between the first and second reflective elements 13, 14 using a user input (not shown).

As shown in FIG. 2 and FIG. 3, a laser treatment device 20 comprises the optical system 1. The laser treatment device 20 may be used to, for example, but not limited to, cut hair 21 extending from a skin surface 22.

The laser treatment device 20 comprises a housing 23. The housing 23 may comprise a guard 24. The guard 24 may be a hair and skin manipulation module. The housing 23 has a skin engaging face 25. The skin engaging face 25 is configured to be placed against the skin surface 22. The skin surface 22 may be, for example, but not limited to, the face or leg of a user or person being treated.

The skin engaging face 25 comprises a recess 26. The centre of the recess 26 is concentric with the centre of the skin engaging face 25. The recess 26 is an oval slit. However, it will be understood that the shape of the cross-section of the recess 26 is not limited thereto. The recess 26 is greater than or equal to 0.3 mm and less than or equal to 1.5 mm wide in the direction of the shaving stroke. The recess width helps to control the doming of the skin surface 22 into the laser treatment device 20. In the present embodiment, the width of the recess 26 is 0.8 mm. The skin engaging face 25 lies in a plane 27 that extends across the recess 26.

The optical system 1 is located within the housing 23 of the laser treatment device 20. The optical system 1 is located at least partially within the recess 26. The recess 26 comprises a cutting zone 28. When the skin engaging face 25 of the laser treatment device 20 is placed against the skin surface 22 and moved along it, the skin surface 22 and any hairs 21 on the skin surface may extend into the cutting zone 28.

The optical system 1 directs the laser pulses across the recess 26 so that part of the treatment pulse optical path 2 is parallel and spaced from the plane 27 which extends across the skin engaging face 25. The treatment pulse optical path 2 is proximate to the plane 27 which extends across the recess 26. Therefore, when the skin engaging face 25 of the laser treatment device 20 is placed against the skin surface 22, at least part of the treatment pulse optical path 2 is proximate the skin surface 22. The treatment pulse, when emitted, may cut the hairs 21 extending from the skin surface 22.

In the present embodiment, the probe pulse is emitted by the laser pulse generating arrangement 3 and is initially directed downwards towards the skin surface 22. The laser pulse generating arrangement 3 directs the probe pulse to the collimating lens 25 which reduces the divergence of the probe pulse. The collimated probe pulse then passes through the focus lenses 12 which align the probe pulse so that it continues on the probe pulse optical path, which may coincide with the treatment pulse optical path 2.

The first reflective element 13, positioned on one side of the recess 26, is configured to reflect the incident probe pulse across the cutting zone 28 of the recess 26. That is, the first reflective element 13 is configured to reflect the incident probe pulse across the cutting zone 28 on the probe pulse optical path which is substantially parallel to and space from the plane 27 which extends across the recess 26 of the laser treatment device 20. Therefore, the probe pulse optical path does coincide with the treatment pulse optical path 2.

The second reflective element 14, positioned on the opposite side of the recess 26, is configured to reflect the probe pulse away from the cutting zone 28. The second reflective element 14 is configured to reflect the probe pulse away from the skin surface 22. The probe pulse is directed towards the detector lens 15 and laser pulse sensor 8 by the second reflective element 14.

The laser pulse sensor 8 generates information indicative of the condition of the probe pulse optical path which coincides with the treatment pulse optical path 2 through the optical system 1 and communicates it to the controller 5. The controller 5 determines the value for at least one of the optical characteristics of the probe pulse and compares it to the expected value.

If the treatment pulse optical path 2 is contaminated, i.e. a surface of one of the components of the optical system 1 has a contaminant on it that directs the probe pulse along an altered optical path 4 or an obstruction 9 such as the skin surface 22 blocks the probe pulse, then the determined value will not fall in the allowable range. Therefore, the controller 5 does not activate the laser pulse generating arrangement 3 to emit the treatment pulse to avoid causing damage or irritation.

If the treatment pulse optical path 2 is not contaminated or obstructed then the values will match and the controller 5 will activate the laser pulse generating arrangement 3 to emit the treatment pulse which will travel along the intended optical path 2 and cut the hairs 21 extending from the skin surface 22.

The optical system 1 may be programmed to know the difference between hair and/or skin and an obstruction 9. For example, the controller 5 may be able to determine the profile of hair and/or skin.

In shaving systems, the at least one sensor 8 may be capable of generating information capable of identifying obstructions caused by hairs 21 to be cut from other obstructions 9, such as skin surfaces 22 or water droplets. For example, a multi-element imaging sensor may be able to identify hair 21 and avoid false positives by comparing the cylindrical shape of a hair 21 to the flat plane of a skin surface 22.

In an alternative example, an intensity sensor may know the intensity drop caused by a hair 21 and will prevent the generation of the treatment pulse if the intensity drops below a predetermined level. In another alternative embodiment, the at least one sensor 8 may measure the temporal profile of a characteristic. The temporal profile of hair 21 will change quickly as the hair 21 is cut, whilst skin or water droplet obstruction 9 will remain in the probe pulse optical path for a longer amount of time. Therefore, the optical system 1 may be able to distinguish hair 21 from the skin surface 22 and/or obstructions 9.

In skin treatment systems, the at least one sensor 8 may be a skin position sensor. The skin position sensor may be capable of generating information indicative of the skin surface's location and geometry. Variations in the skin surface's location and geometry occur in the order of milliseconds to seconds. The variations in spatial and temporal distributions may be used to distinguish the skin surface 22 from hair 21 and/or obstructions 9.

In an alternative embodiment, the at least one characteristic of the probe pulse may be determined before the section of the optical path in which hair 21 and/or skin surface 22 is placed, for example, immediately before the probe pulse travels across the recess 26 parallel to the plane 27 that extends across the recess 26. Therefore, a treatment probe may be released to sever hair when the hair 21 is the only "obstruction" on the optical path 2.

However, the optical system 1 is not limited to being used to cut hair. Alternatively, the optical system 1 may be used in any situation in which a probe pulse is emitted to check that there are no obstructions 9 on the optical path before a hazardous treatment pulse is emitted along the optical path 2.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. An optical system comprising:
   a plurality of optical components;
   a pulse generating arrangement configured to generate (i) a treatment pulse along a treatment pulse optical path through said optical components and (ii) a probe pulse, different from the treatment pulse, along a probe pulse optical path extending through said optical components, wherein at least a portion of the probe pulse optical path is (a) identical to and coincides with the treatment pulse optical path or (b) parallel to and spaced from the treatment pulse optical path as an alternative probe pulse optical path indicative of the treatment pulse optical path;
   a sensor configured to generate information indicative of an optical characteristic of said probe pulse that has passed along said probe pulse optical path through said optical components;
   wherein said information generated by said sensor is indicative of (i) contaminants on a surface of said optical components along said probe pulse optical path which are not to be subject to treatment via the treatment pulse in said treatment pulse optical path, and (ii) desired obstructions which are to be subject to treatment via the treatment pulse in said treatment pulse optical path; and
   a controller configured to control said pulse generating arrangement to generate the probe pulse as a first laser pulse and the treatment pulse as a second laser pulse, subsequent the first laser pulse by a time delay, the controller further being configured to activate said pulse generating arrangement to generate the treatment pulse as the second laser pulse and emit said treatment pulse along the treatment pulse optical path only in response to the information generated by said sensor being indicative of an absence of contaminants on the surface of said optical components in said treatment pulse optical path.

2. The optical system according to claim 1, wherein the contaminants include (i) a contaminant that includes one or more of detritus, a water droplet, and a sweat droplet, or (ii) a skin surface.

3. The optical system according to claim 1, wherein said pulse generating arrangement is configured to generate a treatment pulse having a pulse energy which is greater than the pulse energy of said probe pulse.

4. The optical system according to claim 1, wherein said probe pulse optical path is configured to coincide with at least a part of said treatment pulse optical path.

5. The optical system according to claim 1, wherein said pulse generating arrangement comprises a treatment pulse generator configured to generate said treatment pulse and a probe pulse generator configured to generate said probe pulse.

6. The optical system according to claim 1, wherein the pulse generating arrangement is configured to generate the treatment pulse within 10 ms of the probe pulse.

7. The optical system according to claim 1, wherein the pulse generating arrangement is configured to generate successive probe pulses with a time gap of less than 10 ms.

8. The optical system according to claim 1, wherein the controller is configured to compare the characteristic measured by the sensor to a predetermined value and to emit the treatment pulse as the second laser pulse if the sensed characteristic matches the predetermined value.

9. The optical system according to claim 1, wherein the controller is configured to compare the characteristic measured by the sensor to a predetermined range and to emit the treatment pulse as the second laser pulse if the sensed characteristic falls within said predetermined range.

10. The optical system according to claim 1, wherein the sensor is at an end of the optical path.

11. A laser treatment device comprising the optical system according to claim 1.

12. The laser treatment device according to claim 11, wherein a part of said treatment pulse optical path is across a recess in said laser treatment device, parallel to, and spaced at or away from, a plane that extends across said recess in which a skin engaging face lies.

13. The optical system according to claim 1, wherein said pulse generating arrangement comprises a treatment pulse generator configured to generate said treatment pulse and a probe pulse generator configured to generate said probe pulse.

14. The optical system according to claim 1, wherein the pulse generating arrangement is configured to generate the treatment pulse within 10 ms of the probe pulse.

15. A method for cutting hair using a laser treatment device, having a recess into which hair extends, comprising:
   operating an optical system to direct a probe pulse, different from a treatment pulse, along a probe pulse optical path extending through a plurality of optical components, wherein at least a portion of the probe pulse optical path is (a) identical to and coincides with a treatment pulse optical path or (b) parallel to and spaced from the treatment pulse optical path as an alternative probe pulse optical path indicative of the treatment pulse optical path, further wherein the probe pulse is a first laser pulse, and the treatment pulse is a second laser pulse, subsequent to the first laser pulse by a time delay;
   generating information indicative of a condition of the treatment pulse optical path that also extends through said optical components by measuring a characteristic of said probe pulse, via a sensor, along said probe pulse optical path;
   comparing, via a controller, the measured characteristic of said probe pulse against a predetermined range, wherein the measured characteristic being within the predetermined range corresponds to a presence of desired obstructions which are to be subject to the treatment pulse in said treatment pulse optical path, else outside the predetermined range corresponds to a presence of contaminants on a surface of said optical components along said probe pulse optical path which are not to be subject to the treatment pulse in said treatment pulse optical path; and
   emitting, via the controller configured to activate a pulse generating arrangement of the optical system, the treatment pulse as the second laser pulse, subsequent the first laser pulse by the time delay, along said treatment pulse optical path through said optical components to cut hair extending into said recess only in response to said information being indicative of the characteristic of said probe pulse falling within said predetermined range.

16. A non-transient computer readable medium embodied with a computer program comprising instructions which, when executed by at least one processor, cause the processor to perform the method of claim 15.

17. An optical system comprising:
   a plurality of optical components;
   a pulse generating arrangement configured to generate (i) a treatment pulse along a treatment pulse optical path through said optical components and (ii) a probe pulse, different from the treatment pulse, along a probe pulse optical path extending through said optical components, wherein at least a portion of the probe pulse optical path is (a) identical to and coincides with the treatment pulse optical path or (b) parallel to and spaced from the treatment pulse optical path indicative of the treatment pulse optical path;
   a sensor configured to generate information indicative of an optical characteristic of said probe pulse in response to the probe pulse having passed along said probe pulse optical path through said optical components, wherein said information generated by said sensor is indicative of a presence or an absence of an obstruction in the treatment pulse optical path that obstructs, interrupts, or alters the treatment pulse optical path, wherein the obstruction includes one or more of (i) contaminants on a surface of said optical components along said probe pulse optical path which are not to be subject to treatment via the treatment pulse in said treatment pulse optical path and (ii) desired obstructions which are to be subject to treatment via the treatment pulse in said treatment pulse optical path; and
   a controller configured to control said pulse generating arrangement to generate the probe pulse as a first laser pulse and the treatment pulse as a second laser pulse, subsequent the first laser pulse by a time delay, wherein the controller is further configured to activate said pulse generating arrangement to generate the treatment pulse as the second laser pulse and emit the treatment pulse along the treatment pulse optical path only in response to the information generated by the sensor being indicative of an absence of contaminants on the surface of said optical components in the treatment pulse optical path.

18. The optical system according to claim 17, wherein the contaminants include one or more of detritus, a water droplet, and a sweat droplet.

19. The optical system according to claim 17, wherein the pulse generating arrangement is configured to generate successive probe pulses with a time gap of less than 10 ms.

20. The optical system according to claim 17, wherein the controller is configured to compare the characteristic measured by the sensor to at least one selected from the group consisting of (i) a predetermined value and to emit the treatment pulse as the second laser pulse if the sensed characteristic matches the predetermined value, and (ii) a predetermined range and to emit the treatment pulse as the second laser pulse if the sensed characteristic falls within said predetermined range.

* * * * *